United States Patent
Pröls et al.

(10) Patent No.: US 11,850,252 B2
(45) Date of Patent: Dec. 26, 2023

(54) USE OF NOR-URSODEOXYCHOLIC ACID FOR REDUCING LIVER FAT

(71) Applicant: Dr. Falk Pharma GmbH, Freiburg (DE)

(72) Inventors: Markus Pröls, Freiburg/Breisgau (DE); Roland Greinwald, Kenzingen (DE); Michael Trauner, Vienna (AT); Peter Fickert, Graz (AT)

(73) Assignee: DR. FALK PHARMA GMBH, Freiburg (DE)

( * ) Notice: Subject to any disclaimer, the term of this patent is extended or adjusted under 35 U.S.C. 154(b) by 7 days.

(21) Appl. No.: 16/652,044

(22) PCT Filed: Sep. 28, 2018

(86) PCT No.: PCT/EP2018/076461
§ 371 (c)(1),
(2) Date: Mar. 28, 2020

(87) PCT Pub. No.: WO2019/063790
PCT Pub. Date: Apr. 4, 2019

(65) Prior Publication Data
US 2020/0246357 A1 Aug. 6, 2020

(30) Foreign Application Priority Data
Sep. 28, 2017 (EP) ...................................... 17193777

(51) Int. Cl.
*A61K 31/575* (2006.01)
*A61P 1/16* (2006.01)
*A61K 45/06* (2006.01)

(52) U.S. Cl.
CPC .............. *A61K 31/575* (2013.01); *A61P 1/16* (2018.01); *A61K 45/06* (2013.01)

(58) Field of Classification Search
CPC ................................. A61P 1/16; A61K 31/517
USPC ....................................................... 514/182
See application file for complete search history.

(56) References Cited

U.S. PATENT DOCUMENTS

2018/0031585 A1* 2/2018 Dennis .................... G01N 33/88

FOREIGN PATENT DOCUMENTS

WO 2006119803 A1 11/2006
WO 2012072689 A1 6/2012

OTHER PUBLICATIONS

Beraza et al. "Nor-ursodeoxycholic acid reverses hepatocyte-specific nemo-dependent steatohepatitis" Gut, 2011, vol. 60, pp. 387-396 (Year: 2011).*
Bonekamp et al. "Spatial distribution of MRI-Determined hepatic proton density fat fraction in adult with nonalcoholic fatty liver disease," J. Magnetic Resonance Imaging, 2014, vol. 39, pp. 1525-1532 (Year: 2014).*
Fernadez-Miranda et al. "A pilot trial of fenofibrate for the treatment of non-alcoholic fatty liver disease," Digestive and Liver Disease , 2008, vol. 40. pp. 200-225 (Year: 2008).*
EudraCT No. 2013-004605-38 https://www.clinicaltrialsregister.eu/ctr-search/trial/2013-004605-38/results 2022 (Year: 2022).*
Steinacher et al. "Therapeutic mechanisms of bile acids and Nor-Ursodeoxycholic acid in N0n-alcoholic fatty liver disease," Digestive Diseases, 2017, vol. 35, No. 3, pp. 282-287 (Year: 2017).*
Wyness The four stages of Non-Alcoholic fatty liver Disease (NAFLD) https://www.liverhealthuk.com/post/the-four-stages-of-nafld (Year: 2020).*
Troisi et al. "The treatment with Ursodeoxycholic acid in elderly patients affected by NAFLD and metabolic syndrome: A case-control study," La Clinica Terapeutica, 2013, vol. 163, No. 3, 203-207. Abstract. http://www.seu-roma.it/riviste/clinica_terapeutica/apps/autos.php?id=1140 (Year: 2013).*
Emina Halilbasic, Nor-Ursodeoxycholic Acid as a Novel Therapeutic Approach for Cholestatic and Metabolic Liver Diseases, Digestive Diseases, Bile Acid Receptors and Bile Acid Signaling as Therapeutic Targets, 2017, pp. 288-292, vol. 35, Karger AG, Basel.
Daniel Steinacher, NorUDCA improves liver injury and metabolic situation in mouse models of obesity and steatosis, Journal of Hepatology, Poster Presentations, THU-385, 2017, p. S168, vol. 66, Issue 1, Elsevier Science BV.
Daniel Steinacher, NorUDCA reduces liver injury and improves glucose sensitivity in a mouse model of obesity and steatosis, Journal of Hepatology, vol. 62, Issue 1, Oct. 2015, p. 689A, Wiley-Blackwell.
EB Belonovskaia, Preventative administration of new UDCA derivatives in experimental alcoholic steatohepatitis, Eksperimental'nayal Klinicheskaya Farmakologiya, 2013, pp. 25-29, vol. 69, Issue 1, Russia, ISSN 0869-2092.
Mad Ratziu, Treatment of NASH with ursodeoxyycholic acid: Pro, Clinics and Research in Hepatology and Gastroenterology, Sep. 2012, pp. S41-S45, vol. 36, Elsevier Masson.
The European Union Clinical Trials Register, record entered Dec. 2, 2014, EudraCT No. 2013-004605-38, located at www.clinicaltrialsregister.eu/ctr-search/trial/2013-004605-36/DE.

(Continued)

*Primary Examiner* — Shengjun Wang

(74) *Attorney, Agent, or Firm* — Curatolo Sidoti & Trillis Co., LPA; Floyd Trillis, III; Salvatore A. Sidoti

(57) ABSTRACT

The present invention relates to the use of Nor-UDCA in the treatment of hepatic steatosis in patients having a hepatic fat fraction of greater than 10%.

16 Claims, No Drawings

(56) References Cited

OTHER PUBLICATIONS

International Search Report for Application No. PCT/EP2018/076461, dated Jan. 3, 2019.
International Written Opinion for Application No. PCT/EP2018/076461, dated Jan. 3, 2019.
Takashi Shida, et al., "Usefulness of Noninvasive Diagnostic Procedure for Non-Alcoholic Fatty Liver Disease by Measurement of Hepatic Lipid Content Using Controlled Attenuation Parameter", Sonographic Technology, vol. 30, No. 2, 2015.
A. Fickert et al., "norUrsodeoxycholic acid improves cholestasis in primary sclerosinhg cholangitis", J. Hepatol. 2017, 57, 549-558.

* cited by examiner

USE OF NOR-URSODEOXYCHOLIC ACID FOR REDUCING LIVER FAT

CROSS REFERENCE TO REALTED APPLICATIONS

This application is a national stage application under 35 U.S.C. § 371 of PCT International Patent Application No. PCT/EP2018/076461, filed Sep. 28, 2018, which claims priority from European Patent Application No. 17193777.4, filed Sep. 28, 2017, both of which are hereby incorporated by reference in their entireties.

BACKGROUND OF THE INVENTION

Hepatic steatosis is a condition where excessive fat accumulates in liver cells via the process of steatosis (i.e., abnormal retention of lipids within a cell). Hepatic steatosis can have multiple causes, e.g. excessive alcohol consumption, drug toxicity, metabolic disorders or nutritional reasons.

Hepatic steatosis may convert into a progressive inflammation of the liver (hepatitis), called steatohepatitis. This more severe condition may be termed either alcoholic steatohepatitis or non-alcoholic steatohepatitis (NASH). In more severe stages, patients suffering from NASH may develop liver fibrosis and eventually cirrhosis.

Current options for the therapeutic management of hepatic steatosis are limited. Mainly, dietary changes and life style modifications including weight reduction and increase in physical activity are recommended. No safe and effective medication is available for maintenance therapy that is able to prevent progression of the disease to NASH. Various drugs have been or are being investigated. A positive effect has been observed for pioglitazone, suggesting improvement of steatosis.

Ursodeoxycholic acid (UDCA), a naturally occurring bile acid, which can be found in small amounts in the bile and in the blood of humans, is a widely used drug to treat liver diseases. One of the most important indication areas of UDCA is the dissolution of gallstones and the treatment of primary biliary cirrhosis (PBC). UDCA has cytoprotective, membrane stabilizing and anti-apoptotic effects.

The derivative 24-nor-ursodeoxycholic acid (Nor-UDCA) is a UDCA analog with modified physicochemical properties. Although both substances are structurally related, Nor-UDCA and UDCA show different characteristics when administered to mammals. In contrast to UDCA, Nor-UDCA is a poor substrate for acyl coenzyme A synthetase and undergoes only minimal N-acyl amidation with taurine or glycine. In vivo experiments demonstrated the efficacy of Nor-UDCA in animal models of cholestatic liver disease (WO 2006/119803 A1). In addition, WO 2006/119803 A1 reports an anti-inflammatory activity of Nor-UDCA and consequently claims the use of Nor-UDCA for treating various forms of hepatitis, including alcoholic steatohepatitis, non-alcoholic steatohepatitis and virally induced hepatitis.

Halibasic et al. (2017) Dig Dis 35:288-292 summarizes the recent progress of Nor-UDCA as a novel therapeutic approach in cholestatic and metabolic liver disorders with specific focus on primary sclerosing cholangitis (PSC).

Steinacher et al. (2017) Journal of Hepatology vol. 66; S95-S332; Abstract THU-385, reports that Nor-UDCA improves liver injury and metabolic situation in mouse models of obesity and steatosis. This reference describes a considerable reduction in ALT. In the mouse model used, however, the animals typically have very high levels of ALT. Therefore, it appears unlikely that the ALT levels were actually reduced to levels around the upper limit of normal (ULN) or less.

Steinacher et al. (2015) Hepatology vol. 62 number 1 (Suppl.) page 689A, Abstract 977, reports that Nor-UDCA reduces liver injury and improves glucose sensitivity in a mouse model of obesity and steatosis. In the mouse model used the animals typically have very high levels of ALT. This reference describes a significant reduction in ALT. In the mouse model used, however, the animals typically have very high levels of ALT. Therefore, it appears unlikely that the ALT levels were actually reduced to levels around the upper limit of normal (ULN) or less.

Belonovskaya et al. (2013) Eksperimental'naya I Klinicheskaya Farmakologiya vol. 76, no. 1:25-29, investigated preventive administration of new UDCA derivatives in experimental alcoholic steatohepatitis. It was found that Nor-UDCA was most effective as compared to UDCA in preventing the accumulation of triglycerides in the liver. This reference does not concern treatment of steatosis but is related to the prophylactic effect of UDCA derivatives on the development of experimental alcoholic steatohepatitis.

Ratziu (2012) Clinics and Research in Hepatology and Gastroenterology vol. 15, no. 2: S41-S45 discusses treatment of NASH with UDCA. Ratziu et al. further mentions that new UDCA derivatives have shown promising activity in preclinical models and may be worth testing in clinical trials.

There is a need for a therapeutic treatment of hepatic steatosis which has not yet progressed to steatohepatitis.

SUMMARY OF THE INVENTION

The inventors of this application surprisingly found that administration of Nor-UDCA can significantly reduce liver fat. Nor-UDCA is therefore suitable for reducing the hepatic fat fraction in patients suffering from hepatic steatosis. In particular, this effect is also present in patients that do not yet have signs of inflammation or hepatitis. In addition, it was found that the treatment is most effective if more than 500 mg/day of Nor-UDCA is administered. A further surprising finding was that even patients with mild steatosis and having a level of alanine transaminase (ALT) which is less than the upper limit of normal (ULN) benefited from the protective effect of the treatment. In addition, the inventors found that Nor-UDCA is capable of reducing the serum levels of cytokeratin 18 fragments, which are known as markers of apoptosis or necrosis. The present invention therefore relates to the subject matter defined in the following items [1] to [65]:

[1] Nor-UDCA for use in the treatment of hepatic steatosis, wherein said treatment comprises administering to a human patient an effective amount of Nor-UDCA, and wherein said human patient has a hepatic fat fraction of greater than 10%.
[2] Nor-UDCA for use in the treatment of hepatic steatosis, wherein said treatment comprises administering to a human patient an effective amount of Nor-UDCA.
[3] Nor-UDCA for use according to item 1 or 2, wherein the patient has moderate hepatic steatosis.
[4] The Nor-UDCA for use according to item 1 or 2, wherein the patient has severe hepatic steatosis.
[5] The Nor-UDCA for use according to any one of the preceding items, wherein the patient has a serum concentration of alanine transaminase (ALT) which is less than 4 times the upper limit of normal (ULN), e.g. from 0.8-fold the ULN to less than 4-fold the ULN.

[6] The Nor-UDCA for use according to any one of the preceding items, wherein the patient has a serum concentration of ALT which is less than 3 times the ULN, e.g. from 0.8-fold the ULN to less than 3-fold the ULN.
[7] The Nor-UDCA for use according to any one of the preceding items, wherein the patient has a serum concentration of ALT which is less than 2 times the ULN, e.g. from 0.8-fold the ULN to less than 2-fold the ULN.
[8] The Nor-UDCA for use according to any one of the preceding items, wherein the patient has a serum concentration of ALT which is equal to or less than the ULN, e.g. from 0.8-fold of the ULN to 1-fold of the ULN.
[9] The Nor-UDCA for use according to any one of the preceding items, wherein the patient has a serum concentration of aspartate transaminase (AST) which is less than 4 times the ULN.
[10] The Nor-UDCA for use according to any one of the preceding items, wherein the patient has a serum concentration of AST which is less than 3 times the ULN.
[11] The Nor-UDCA for use according to any one of the preceding items, wherein the patient has a serum concentration of AST which is less than 2 times the ULN.
[12] The Nor-UDCA for use according to any one of the preceding items, wherein the patient has a serum concentration of AST which is equal to or less than the ULN.
[13] The Nor-UDCA for use according to any one of the preceding items, wherein the patient has a hepatic fat fraction of at least 12%, e.g. from 12% to 50%.
[14] The Nor-UDCA for use according to any one of the preceding items, wherein the patient has a hepatic fat fraction of at least 15%, e.g. from 15% to 40%.
[15] The Nor-UDCA for use according to any one of the preceding items, wherein the patient has a hepatic fat fraction of at least 20%, e.g. from 20% to 30%.
[16] The Nor-UDCA for use according to any one of the preceding items, wherein the hepatic fat fraction is determined by magnetic resonance imaging or magnetic resonance spectroscopy (MRS).
[17] The Nor-UDCA for use according to any one of the preceding items, wherein said treatment reduces the hepatic fat fraction of the patient by at least 1 percentage point.
[18] The Nor-UDCA for use according to any one of the preceding items, wherein said treatment reduces the hepatic fat fraction of the patient by at least 2 percentage points.
[19] The Nor-UDCA for use according to any one of the preceding items, wherein said treatment reduces the hepatic fat fraction of the patient by at least 3 percentage points.
[20] The Nor-UDCA for use according to any one of the preceding items, wherein said treatment reduces the hepatic fat fraction of the patient by at least 4 percentage points.
[21] The Nor-UDCA for use according to any one of the preceding items, wherein said treatment reduces the hepatic fat fraction of the patient by at least 5 percentage points.
[22] The Nor-UDCA for use according to any one of items 17 to 21, wherein said reduction of the hepatic fat fraction of the patient occurs within 12 weeks.
[23] The Nor-UDCA for use according to any one of the preceding items, wherein the hepatic fat fraction of the patient is determined by Magnetic Resonance Imaging (MRI).
[24] The Nor-UDCA for use according to any one of the preceding items, wherein the body mass index of the patient is greater than 25 kg/m$^2$.
[25] The Nor-UDCA for use according to any one of the preceding items, wherein the body mass index of the patient is greater than 26 kg/m$^2$.
[26] The Nor-UDCA for use according to any one of the preceding items, wherein the body mass index of the patient is greater than 27 kg/m$^2$.
[27] The Nor-UDCA for use according to any one of the preceding items, wherein the body mass index of the patient is greater than 28 kg/m$^2$.
[28] The Nor-UDCA for use according to any one of the preceding items, wherein the body mass index of the patient is greater than 29 kg/m$^2$.
[29] The Nor-UDCA for use according to any one of the preceding items, wherein the body mass index of the patient is greater than 30 kg/m$^2$.
[30] The Nor-UDCA for use according to any one of the preceding items, wherein the patient has liver fibrosis.
[31] The Nor-UDCA for use according to any one of the preceding items, wherein the liver of the patient does not show signs of inflammation and/or wherein the patient does not have hepatitis.
[32] The Nor-UDCA for use according to any one of the preceding items, wherein the dose of Nor-UDCA administered to the patient is from 750 mg/day to 2,500 mg/day.
[33] The Nor-UDCA for use according to any one of the preceding items, wherein the dose of Nor-UDCA administered to the patient is from 1,000 mg/day to 2,000 mg/day, preferably from 1,250 mg/day to 1,750 mg/day, most preferably about 1,500 mg/day.
[34] The Nor-UDCA for use according to any one of the preceding items, wherein the Nor-UDCA is administered to the patient once per day.
[35] The Nor-UDCA for use according to any one of the preceding items, wherein said treatment further comprises administering an active agent different from Nor-UDCA, wherein said active agent different from Nor-UDCA is selected from the group consisting of antifibrotic agents, anti-inflammatory agents, immunomodulators, biologics, cholesterol reducing substances, leukotriene antagonists, PPARα/δ-agonists, CCR2/5-inhibitors, ASBT-inhibitors and combinations thereof.
[36] The Nor-UDCA for use according to item 35, wherein said active agent different from Nor-UDCA is an antifibrotic agent selected from the group consisting of pirfenidone, fibrates, FXR-agonists, and combinations thereof.
[37] The Nor-UDCA for use according to item 35, wherein said active agent different from Nor-UDCA is an anti-inflammatory agent selected from the group consisting of non-steroidal anti-inflammatory drugs (NSAIDs), corticosteroids and combinations thereof.
[38] The Nor-UDCA for use according to item 37, wherein said NSAID is selected from the group consisting of acetylsalicylic acid, celecoxib, dexdetoprofen, diclofenac, diflunisal, etodolac, etoricoxib, fenoprofen, firocoxib, flurbiprofen, ibuprofen, indomethacin, ketoprofen, ketorolac, licofelone, lornoxicam, loxoprofen, lumiracoxib, meclofenamic acid, mefenamic acid, meloxicam, nabumetone, naproxen, nimesulide, oxaporozin, parecoxib, piroxicam, rofecoxib, salsalate, sulindac, tenoxicam, tolfenamic acid, valdecoxib and combinations thereof.
[39] The Nor-UDCA for use according to item 37, wherein said corticosteroid is selected from the group consisting of budesonide, fluticasone, flunisolide, ciclesonide, mometasone, beclomethasone and combinations thereof.
[40] The Nor-UDCA for use according to item 35, wherein said active agent different from Nor-UDCA is an immunomodulator selected from the group consisting of azathioprine, 6-mercaptopurine, cyclosporine A, tacrolimus, methotrexate and combinations thereof.

[41] The Nor-UDCA for use according to item 35, wherein said active agent different from Nor-UDCA is a cholesterol reducing substance selected from the group consisting of statins, cholesterol absorption inhibitors (e.g. ezetimibe), sequestrants, niacin and combinations thereof.
[42] The Nor-UDCA for use according to item 41, wherein said statin is selected from the group consisting of atorvastatin, fluvastatin, lovastatin, pitavastatin, pravastatin, rosuvastatin, simvastatin and combinations thereof.
[43] The Nor-UDCA for use according to item 35, wherein said active agent different from Nor-UDCA is a biologic selected from the group consisting of TNF-alpha antagonists, adhesion molecule antagonists (e.g. vedolizumab, etrolizumab), JAK inhibitors (e.g. tofacitinib) and combinations thereof.
[44] The Nor-UDCA for use according to item 35, wherein said active agent different from Nor-UDCA is an anti-TNF-alpha antagonist selected from the group consisting of adalimumab, infliximab, golimumab, etanercept, certolizumab and combinations thereof.
[45] The Nor-UDCA for use according to item 35, wherein said active agent different from Nor-UDCA is a leukotriene antagonist selected from the group consisting of montelukast, zafirlukast, meclofenamate, zileuton and combinations thereof.
[46] The Nor-UDCA for use according to any one of the preceding items, wherein said Nor-UDCA is administered orally to said human patient.
[47] The Nor-UDCA for use according to any one of the preceding items, wherein said human patient further suffers from diabetes mellitus type 2.
[48] The Nor-UDCA for use according to any one of the preceding items, wherein said human patient further suffers from hypertension.
[49] The Nor-UDCA for use according to any one of the preceding items, wherein said human patient further suffers from hypercholesterolaemia.
[50] The Nor-UDCA for use according to any one of the preceding items, wherein said human patient further suffers from hyperlipidemia.
[51] The Nor-UDCA for use according to any one of the preceding items, wherein said human patient further suffers from dyslipidaemia.
[52] The Nor-UDCA for use according to any one of the preceding items, wherein said human patient further suffers from splenomegaly.
[53] The Nor-UDCA for use according to any one of the preceding items, wherein said human patient further suffers from obesity.
[54] The Nor-UDCA for use according to any one of the preceding items, wherein said Nor-UDCA is a chemically pure polymorph, wherein the total amount of chemical impurities is less than 0.5 wt.-%, and at least 60% of the polymorph particles have a size <10 µm.
[55] The Nor-UDCA for use according to item [54], wherein the total amount of chemical impurities in the polymorph is less than 0.1 wt.-%, preferably less than 0.05 wt.-%.
[56] The Nor-UDCA for use according to item [54] or [55], wherein said polymorph is thermodynamically stable.
[57] The Nor-UDCA for use according to any one of items [54] to [56], wherein said Nor-UDCA is in its anhydrous form.
[58] The Nor-UDCA for use according to any one of items [54] to [57], wherein said polymorph is characterized by XRPD peaks at 11.9, 14.4, 15.3, 15.8, and 16.6±0.2 degrees of 2-theta.
[59] The Nor-UDCA for use according to any one of items [54] to [58], wherein said polymorph is characterized by the XRPD pattern as shown in FIG. 5 of WO 2012/072689 A1.
[60] The Nor-UDCA for use according to any one of items [54] to [59], wherein said polymorph contains no amorphous Nor-UDCA in detectable amount.
[61] The Nor-UDCA for use according to any one of items [54] to [60], wherein said polymorph has a volume-weighted average particle diameter D50 of less than 10 µm.
[62] The Nor-UDCA for use according to any one of items [54] to [61], wherein said polymorph has a volume-weighted average particle diameter D95 of less than 30 µm.
[63] The Nor-UDCA for use according to any one of the preceding items, wherein said human patient is an adult, preferably an adult having an age from 18 to 75.
[64] The use of Nor-UDCA as defined in any one of items [54] to [62] in the manufacture of a medicament for the treatment of steatosis as defined in any one of items [1] to [53] or [63].
[65] Nor-UDCA for use in reducing liver fat, wherein said use optionally comprises a treatment as defined in any one of the preceding items.

DETAILED DESCRIPTION

The present invention relates to the use of Nor-UDCA for the treatment of hepatic steatosis in a patient having a hepatic fat fraction of greater than 10%. The treatment comprises administering to a human patient an effective amount of Nor-UDCA, and optionally at least one further active agent.

Nor-UDCA

As used herein, the term Nor-UDCA refers to the compound 24-nor-ursodeoxycholic acid, which has the following structural formula:

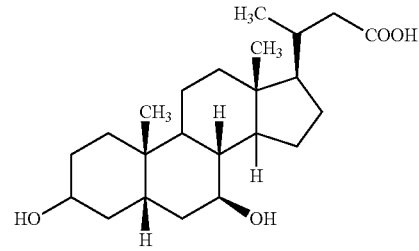

The Nor-UDCA to be used in accordance with this invention and its preparation is not particularly limited. Preferably, the Nor-UDCA is in the form of a crystal prepared as described in WO 2012/072689 A1. In preferred embodiments, a pure polymorph of Nor-UDCA, or of a pharmaceutically acceptable salt thereof, is used. The polymorph is preferably thermodynamically stable. The polymorph of Nor-UDCA or pharmaceutically acceptable salt thereof is typically in its anhydrous form. That is, the polymorph crystals contain substantially no water. The amount of water in the crystals is generally less than 1%, preferably less than 0.5%, more preferably less than 0.1%, based on the total weight of the crystal. The polymorph is typically characterized by XRPD peaks at 11.9, 14.4, 15.3, 15.8, and 16.6±0.2 degrees of 2-theta. Preferably, the polymorph is characterized by the XRPD pattern as shown in FIG. 5 for "Form A" of WO 2012/072689 A1. The disclosure of WO 2012/072689 A1 is expressly referred to herein, and its disclosure is incorporated herein in its entirety.

The polymorph of Nor-UDCA is preferably single-polymorphic, i.e. it essentially consists of a single polymorph, and/or it has polymorphic purity. The amount of amorphous Nor-UDCA in the polymorph is typically negligible. Preferably, no amorphous Nor-UDCA in the polymorph of the present invention is detectable, e.g. by XRPD. More preferably, the polymorph contains substantially no amorphous Nor-UDCA. Most preferably the polymorph of the invention does not contain any amorphous Nor-UDCA. The amount of the polymorph of Form A in the polymorph of the present invention is preferably at least 99%, more preferably at least 99.5%, more preferably at least 99.9%, most preferably substantially 100%, based on the total weight of the Nor-UDCA.

The particle size distribution of the polymorph is preferably such that at least 60% of the crystals have a particle size of less than 10 μm. The polymorph preferably has a D50 of less than 10 μm. For example, the D50 may range from 0.5 μm to 10 μm, more preferably from 1 μm to 9 μm, more preferably from 2 μm to 8 μm, most preferably from 3 μm to 7 μm. The polymorph preferably has a D90 of less than 30 μm. For example, the D90 may range from 2 μm to 30 μm, more preferably from 5 μm to 25 μm, more preferably from 8 μm to 20 μm, most preferably from 10 μm to 18 μm. The polymorph preferably has a D95 of less than 30 μm. For example, the D95 may range from 3 μm to 30 μm, more preferably from 6 μm to 28 μm, more preferably from 9 μm to 25 μm, most preferably from 10 μm to 20 μm.

D50, D90 and D95 represent the median or the 50th percentile, the $90^{th}$ percentile and the 95th percentile of the particle size distribution, respectively, as measured by volume. That is, D50 (D90; D95) is a value on the distribution such that 50% (90%; 95%) of the particles have a volume of this value or less.

The particle size distribution can be determined according the European Pharmacopeia (Ph. Eur.), edition 6.6, section 2.9.31, preferably with a Mastersizer 2000 by Malvern instruments. The evaluation is typically carried out by the Fraunhofer model.

Patients Having Hepatic Steatosis

The human patient to be treated has hepatic steatosis. Hepatic steatosis is defined as the presence of intracellular fat in at least 5% of hepatocytes. More specifically, hepatic steatosis can be defined histologically as a condition when at least 5% of hepatocytes in a tissue section stained with hematoxylin and eosin contain macrovesicular steatosis. Steatosis can be graded from 0 to 3 based on its severity: grade 0 (normal)=<5%; grade 1 (mild)=5%-33%; grade 2 (moderate)=34%-66%; and grade 3 (severe)=at least 67% of hepatocytes characterized by macroscopic steatosis (Kleiner et al., Hepatology 2005, 41, 1313-1321). Hepatic steatosis can be diagnosed by histological examination of a liver biopsy, by ultrasonography, computed tomography, or magnetic resonance imaging.

The patient to be treated in accordance with this embodiment further has a hepatic fat fraction of greater than 10%. The hepatic fat fraction can be determined by MRI or MRS as described in Example 3 herein below. Preferably, the hepatic fat fraction is determined by MRI. The MRI technique is also described in Dixon, W. T., Radiology 1984, 153, 189-194. In a specific embodiment the hepatic fat fraction is the MRI-determined proton density fat fraction (PDFF). This technique provides a quantitative, standardized and objective MRI measurement of hepatic fat based upon inherent tissue properties (see Hines et. al.., "T1 independent, T2* corrected chemical shift based fat-water separation with multi-peak fat spectral modeling is an accurate and precise measure of hepatic steatosis". J. Magn. Reson. Imaging 2011, 33, 873-881; and Meisamy et al., "Quantification of hepatic steatosis with T1-independent, T2*-corrected MR imaging with spectral modeling of fat: blinded comparison with MR spectroscopy". Radiology 2011, 258, 767-775.

In another embodiment, the patient has a hepatic fat fraction of greater than 12%, or greater than 15%, or greater than 20%. For example, the hepatic fat fraction may be at least 16%, or at least 17%, or at least 18%, or at least 19%, or at least 20%, or at least 21%, or at least 22%, or at least 23%, or at least 24%, or at least 25%.

In another embodiment, the patient to be treated has a hepatic triglyceride content, as determined by proton magnetic resonance spectroscopy ($^1$H-MRS), of at least 6%, or at least 8%, or at least 10%, or at least 12%, or at least 15%, or at least 20%. This technique provides an accurate and reproducible measurement of liver fat content (see, e.g. Bohte et al., Eur. Radiol. 2011, 21, 87-97).

Preferably, the disorder to be treated is non-alcoholic hepatic steatosis which is defined as hepatic steatosis not caused by excess alcohol intake (>30 g/day in men and >20 g/day in women), hepatitis B or C, autoimmune hepatitis, iron overload, drugs or toxins.

In one embodiment, the human patient to be treated in accordance with the present invention does not have, or has not been diagnosed as having, alcoholic steatohepatitis or non-alcoholic steatohepatitis. The absence of inflammation in the liver can be determined by histologic examination of a liver biopsy or by non-invasive procedures, e.g. transient elastography.

In another embodiment, the patient does not have, or has not been diagnosed as having, arteriosclerosis.

In another embodiment, the human patient to be treated in accordance with the present invention does not have, or has not been diagnosed as having, a condition selected from the group consisting of primary sclerosing cholangitis (PSC), primary biliary cirrhosis (PBC), progressive familial intrahepatic cholestasis, in particular progressive familial intrahepatic cholestasis type 1, 2 and 3, cystic fibrosis, drug-induced cholestasis, chronic viral hepatitis (B, C, D), alcoholic steatohepatitis, non-alcoholic steatohepatitis, autoimmune hepatitis, hemochromatosis, Wilson disease and alpha-1-antitrypsin deficiency. The diagnosis of these conditions is well known to those of skill in the art.

The patient typically has a serum level of ALT of less than 4 times the upper limit of normal (ULN). Preferably, the serum level of ALT is less than 3 times, or less than 2 times, or equal to or less than the ULN. The ULN for ALT is 50 U/L for male adults and 35 U/L for female adults. Preferably, in the course of the treatment the serum level of ALT is reduced by at least 5%, or by at least 10%, or by at least 15%, or by at least 20%. It is further preferred that, in the course of the treatment, the serum level of ALT is reduced to less than the ULN. In a further preferred embodiment, the serum level of ALT is reduced to ≤0.8 times the ULN in the course of the treatment. In one embodiment the patient to be treated has a serum level of ALT of >1.5 times the ULN, and the treatment reduces the serum level of ALT to less than 1.5 times the ULN. In another embodiment, the patient to be treated has a serum level of ALT of greater than the ULN, and the treatment reduces the serum level of ALT to less than the ULN. In yet another embodiment, the patient to be treated has a serum level of ALT of >0.8 times the ULN, and the treatment reduces the serum level of ALT to less than 0.8 times the ULN.

The term "adults", as used herein, refers to human individuals having an age of at least 18 years. When reference is made herein to a certain effect observed or achieved during the treatment, or "in the course of the treatment", this refers to a treatment period of 12 weeks, unless indicated otherwise.

The patient typically has a serum level of AST of less than 4 times the upper limit of normal (ULN). Preferably, the serum level of AST is less than 3 times, or less than 2 times, or equal to or less than the ULN. The ULN for AST is 50 U/L for male adults and 35 U/L for female adults. Preferably, in the course of the treatment the serum level of AST is reduced to less than the ULN. It is also preferred that in the course of the treatment the serum level of AST is reduced by at least 5%, or by at least 10%, or by at least 15%.

In one embodiment, the patient has a serum level of gamma-glutamyl transpeptidase (GGT) which is greater than the ULN. The ULN for GGT is 71 U/L for male adults and 42 U/L for female adults. Preferably, in the course of the treatment, the serum level of GGT is reduced by at least 5%, or by at least 10%, or by at least 15%, or by at least 20%, or even by at least 25%. In a specific embodiment, in the course of the treatment the serum level of GGT is reduced to less than the ULN.

The patient typically has a serum level of alkaline phosphatase (AP) of less than the ULN. The ULN for AP is 129 U/L for male adults and 104 U/L for female adults. Preferably, the serum level of AP does not increase in the course of the treatment.

In one embodiment, the patient has severe steatosis. In another embodiment, the patient has moderate steatosis. In yet another embodiment, the patient has mild steatosis. The grades of hepatic steatosis (mild, moderate or severe) are defined as described above and can be determined by histologic examination of a liver biopsy.

In the course of the treatment of the invention, the hepatic fat fraction may be reduced to less than 25%, or less than 20%, or less than 18%, or less than 16%, or less than 14%, or less than 12%, or less than 10%, or less than 8%, or less than 6%. In another embodiment, the treatment reduces the hepatic fat fraction by at least 5%, or at least 10%, or at least 15%, relative to the value at the beginning of the treatment. In another embodiment, the treatment reduces the hepatic fat fraction by at least 1% percentage point, or by at least 2% percentage points, or by at least 3% percentage points, or by at least 4% percentage points, or by at least 5% percentage points, relative to the value at the beginning of the treatment. As an example, a reduction of the hepatic fat fraction from 20% to 18% represents a "reduction to 18%", a "reduction by 10%", or a "reduction by 2 percentage points", just to illustrate the difference between the reduction to a certain percentage of liver fat fraction, the reduction in % and reduction in percentage points.

In another embodiment, the patient to be treated has a serum level of cytokeratin 18 (M65) of less than 750 U/ml, or less than 600 U/ml, or less than 500 U/ml, or less than 400 U/ml, or less than 300 U/ml or even less than 250 U/ml. The level of the M65 fragment of cytokeratin-18 can be determined by known methods, e.g. by an enzyme-linked immunosorbent assay (ELISA)

In another embodiment, the patient to be treated has a serum level of cytokeratin 18 (M30) of less than 500 U/ml, or less than 400 U/ml, or less than 300 U/ml, or less than 200 U/ml, or less than 150 U/ml. The level of the M30 fragment of cytokeratin-18 can be determined by known methods, e.g. by an ELISA.

Serum levels of soluble forms of cytokeratin 18 were reported to increase in patients with NASH. Specifically, the cleaved M30 fragment has been recognized as a marker of apoptosis, and the M65 fragment as a marker of necrosis. The inventors found that Nor-UDCA is capable of reducing the serum levels of M30 fragment and M65 fragment.

In the course of the treatment of the invention, the serum level of cytokeratin 18 (M65) may be reduced by at least 3%, or at least 5%, or at least 7%, or at least 10%, relative to the value at the beginning of the treatment.

In the course of the treatment of the invention, the serum level of cytokeratin 18 (M30) may be reduced by at least 3%, or at least 5%, or at least 7%, or at least 10%, relative to the value at the beginning of the treatment.

The patient to be treated is preferably an adult human, more preferably an human patient having an age from 18 to 75.

The human patient to be treated typically has a body weight of from 40 kg to 200 kg, preferably from 50 kg to 150 kg, more preferably from 60 kg to 120 kg.

The patient to be treated typically has a BMI of greater than 25 $kg/m^2$. In other embodiments, the BMI of the patient may be at least 26, or at least 27, or at least 28, or at least 29, or at least 30 $kg/m^2$. The BMI is defined as the body mass divided by the square of the body height, and is universally expressed in units of $kg/m^2$, resulting from mass in kilograms and height in meters.

In one embodiment the patient has a liver stiffness, as determined by acoustic radiation force impulse (ARFI), of stage 2 or higher. This corresponds to a shear wave velocity of greater than 1.34 m/s. The stages of liver stiffness as determined by ARFI are defined in example 2 below. In another embodiment, the patient has a liver stiffness, as determined by ARFI, of stage 3 or higher. In yet another embodiment, the patient has a liver stiffness, as determined by ARFI, of stage 4. In yet another embodiment, in the course of the treatment, the liver stiffness, as determined by ARFI, is reduced by one stage (i.e. from stage 2 to stage 0/1, or from stage 3 to stage 2, or from stage 4 to stage 3). Preferably, the liver stiffness, as determined by ARFI, is reduced in the course of the treatment to stage 0/1. In a specific embodiment, the patient has stage 2 prior to the treatment, and stage 0/1 at the end of the treatment.

ARFI is a sonographic technique that determines the local mechanical properties of tissue, e.g. of the liver. Short-duration acoustic pulses are subsequently generated in the vicinity of a designated region of interest. The corresponding localized mechanical excitation of tissue results in tissue displacement and the formation of a shear wave away from the site of excitation. The velocity of the wave propagation, expressed in meters per second, is calculated and allows assessment of the viscoelastic properties of the liver tissue. The more elastic the tissue, the greater degree of displacement it undergoes. This allows a quantitative assessment, as the shear wave propagation velocity is proportional to the square root of tissue elasticity; therefore, the stiffer the liver, the higher the recorded shear wave velocity. A high stiffness is indicative of poor liver health status.

Pharmaceutical Compositions and Treatment

The Nor-UDCA is typically administered in the form of a pharmaceutical composition which may comprise one or more suitable excipients which are pharmaceutically acceptable.

The Nor-UDCA can be formulated for oral administration, wherein these formulations further comprise pharmaceutically acceptable carriers, adjuvants, excipients and/or vehicles.

Solid dosage forms for oral administration can include tablets, preferably effervescent or chewable tablets, capsules, pills, powders and granules. In such solid dosage forms, the Nor-UDCA can be admixed with regularly used substances like sucrose, mannitol, sorbitol, starch and starch derivatives, cellulose and cellulose derivates (e.g., microcrystalline cellulose), di-calcium phosphate, lactose, colloidal anhydrous silica, talc, lubricating agents (e.g. magnesium stearate, macrogols), disintegrants and buffering agents. Tablets and pills can also be prepared with enteric coatings in order to prevent that Nor-UDCA is affected by the stomach acids and enzymes.

The dosage forms comprising the Nor-UDCA can further include conventional excipients, preferably pharmaceutically acceptable organic or inorganic carrier substances which do not react with the active compound. Suitable pharmaceutically acceptable carriers include, for instance, water, salt solutions, alcohol, oils, preferably vegetable oils, polyethylene glycols, gelatin, lactose, amylose, magnesium stearate, surfactants, perfume oil, fatty acid mono-glycerides and diglycerides, petroethral fatty acid esters, hydroxymethyl-cellulose, polyvinylpyrrolidone and the like. The pharmaceutical preparations can be sterilized and if desired, mixed with auxiliary agents, like lubricants, preservatives, stabilizers, wetting agents, emulsifiers, salts for influencing osmotic pressure, buffers, colorings, flavouring and/or aromatic substances and the like which do not deleteriously react with the active compounds. For parenteral application, particularly suitable vehicles consist of solutions, preferably oily or aqueous solutions, as well as suspensions, emulsions, or implants.

Various delivery systems are known and can be used to administer the Nor-UDCA, including, for example, encapsulation in liposomes, emulsions, microparticles, microcapsules and microgranules. The required dosage can be administered as a single unit or in a sustained release form. The required dosage form may further be administered in a multiple unit dosage form, in immediate, sustained, prolonged, or extended release form, prepared by coating, as a matrix formulation and the like.

The bioavailability of the Nor-UDCA may be enhanced by micronization of the formulations using conventional techniques such as grinding, milling and spray drying in the presence of suitable excipients or agents such as phospholipids or surfactants. However, in a special embodiment no grinding and milling is required as the Nor-UDCA polymorph of the invention already has a suitable particle size.

The Nor-UDCA may be formulated in a pharmaceutically acceptable salt form. Pharmaceutically acceptable salts of the Nor-UDCA include preferably metal salts, in particular alkali metal salts, or other pharmaceutically acceptable salts. Pharmaceutically acceptable base addition salts include metallic salts made from lithium, calcium, magnesium, potassium, sodium and zinc or organic salts made from primary, secondary and tertiary amines and cyclic amines.

The pharmaceutical composition comprises preferably an effective amount of Nor-UDCA and a pharmaceutically acceptable carrier and/or excipient.

The dose of the Nor-UDCA is not particularly limited. However, doses of more than 500 mg per day are preferred, e.g. 750-2,500 mg/day, or 1,000 to 2,000 mg per day, or 1,250 to 1,750 mg per day, e.g. 1,500 mg per day. Said amounts are administered preferably at once or possibly in more than one dose (at least 2, 3, 4, 5 or 10 doses) per day. The drug or the pharmaceutical composition may be administered for more than one week, preferably more than four weeks, more preferably more than six months, most preferably more than one year, in particular until resolution of hepatic steatosis.

Combination Therapy

Nor-UDCA or salts thereof can be administered not only in combination with pharmaceutically acceptable carriers and in dosage forms as described herein, but, of course, also in combination with one or more additional active ingredients (e.g. ursodeoxycholic acid, NSAID, like sulindac and ibuprofen) which are also known to be effective against the same or a similar disease to be treated (e.g. ursodeoxycholic acid) or against another disease, which may be preferably a result of a liver disease, or of a condition such as metabolic syndrome or diabetes mellitus type 2.

The combination treatment in accordance with the present invention may comprise administering the active agents in admixture or as separate dosage forms. The combination treatment may comprise administering the active agents simultaneously or in a timely separated manner, e.g. sequentially.

The treatment may comprise administering an active agent different from Nor-UDCA, wherein said active agent different from Nor-UDCA is selected from the group consisting of antifibrotic agents, anti-inflammatory agents, immunomodulators, biologics, cholesterol reducing substances, leukotriene antagonists and combinations thereof.

Suitable antifibrotic agents include, but are not limited to, cenicriviroc, elafibranor, pirfenidone, fibrates, FXR agonists (e.g. obeticholic acid) and combinations thereof. Fibrates include, but are not limited to, aluminium clofibrate, bezafibrate, ciprofibrate, choline fenofibrate, clinofibrate, clofibrate, clofibride, fenofibrate, gemfibrozil, ronifibrate, simfibrate and combinations thereof.

Suitable anti-inflammatory agents include, but are not limited to, NSAIDs, corticosteroids and combinations thereof. The NSAID may be selected from the group consisting of acetylsalicylic acid, celecoxib, dexdetoprofen, diclofenac, diflunisal, etodolac, etoricoxib, fenoprofen, firocoxib, flurbiprofen, ibuprofen, indomethacin, ketoprofen, ketorolac, licofelone, lornoxicam, loxoprofen, lumiracoxib, meclofenamic acid, mefenamic acid, meloxicam, nabumetone, naproxen, nimesulide, oxaporozin, parecoxib, piroxicam, rofecoxib, salsalate, sulindac, tenoxicam, tolfenamic acid, valdecoxib and combinations thereof. The corticosteroid may be selected from the group consisting of budesonide, fluticasone, flunisolide, ciclesonide, mometasone, beclomethasone and combinations thereof.

Suitable immunomodulators include, but are not limited to, azathioprine, 6-mercaptopurine, cyclosporine A, tacrolimus, methotrexate and combinations thereof.

Suitable biologics include, but are not limited to, TNF-alpha antagonists (e.g. adalimumab, infliximab, golimumab, etanercept, or certolizumab), adhesion molecule antagonists (e.g. vedolizumab, etrolizumab), JAK inhibitors (e.g. tofacitinib) and combinations thereof.

Suitable cholesterol reducing substances include, but are not limited to, statins, cholesterol absorption inhibitors (e.g. ezetimibe), sequestrants, niacin and combinations thereof. Suitable statins include, but are not limited to, atorvastatin, fluvastatin, lovastatin, pitavastatin, pravastatin, rosuvastatin, simvastatin and combinations thereof.

Suitable leukotriene antagonists may include, but are not limited to, montelukast, zafirlukast, meclofenamate, zileuton and combinations thereof.

Another aspect of the invention is the use of Nor-UDCA for reducing liver fat. The preferred embodiments of this aspect correspond to the preferred aspect described for other aspects of the invention hereinabove.

Yet another aspect of the invention is a method for reducing liver fat, comprising to a patient in need thereof an effective amount of Nor-UDCA. The preferred embodiments of this aspect correspond to the preferred aspect described for other aspects of the invention hereinabove.

EXAMPLES

A double-blinded, randomized, placebo-controlled phase II clinical trial was conducted as described in the following.

Main Inclusion Criteria:

NAFLD, defined by at least 1 of the following 3 criteria:
(1) Hepatic steatosis demonstrated by ultrasound (at least stage 1) or other diagnostic imaging techniques such as magnetic resonance imaging (MRI), chemical shift imaging (CSI) and/or magnetic resonance spectroscopy (MRS) (fat fraction >10%) within the last 4 weeks (2) At least grade 1 (>10%) steatosis in CAP (controlled attenuation parameter) Fibroscan within the last 4 weeks (3) Diagnostic histological findings shown on prior biopsy within the last 5 years

ALT>0.8 ULN

Patients with diabetes mellitus type 2 must have been diagnosed by at least one of the following ADA criteria:
(1) Random plasma glucose concentration >200 mg/dl
(2) Fasting plasma glucose >126 mg/dl (7.0 mmol/l),
(3) 2 h post-dose glucose >200 mg/dl during a 75 g oral glucose tolerance test
(4) HbA1c≥6.5%

Main Exclusion Criteria:

History of significant (>20 g/d in females, >30 g/d in males on average) alcohol consumption for a period of more than 3 consecutive months within 1 year prior to screening, or history of alcoholic disease History or presence of other concomitant liver diseases including:
Positive hepatitis B or C serology (HBs Ag+, anti-HBc+, anti-HCV+; patients who presented with anti-HBc+ only, could be included if they were HBV-DNA negative)
Primary biliary cirrhosis (AMA-positive)
Primary sclerosing cholangitis
Wilson's disease
Haemochromatosis
Autoimmune hepatitis
α1AT deficiency
Known bile duct obstruction
Drug induced liver disease
Suspected or proven liver cancer
Presence of cirrhosis >Child-Pugh Score A
Uncontrolled diabetes mellitus defined as HbA1c≥9.5% at screening and/or baseline visit
AST or ALT>4×ULN at screening and/or baseline visit Patients with a clinical diagnosis of non-alcoholic hepatic steatosis were randomized to a 12-week treatment period and a 4-week follow-up. Patients were divided into three groups. The first groups received 1,500 mg Nor-UDCA per day (6 capsules with 250 mg Nor-UDCA in each capsule). The second group received 500 mg Nor-UDCA per day (2 capsules with 250 mg Nor-UDCA in each capsule and 4 capsules with 250 mg placebo in each capsule). The third group received 6 capsules with 250 mg placebo in each capsule.

The Nor-UDCA was prepared as described in WO 2012/072689 A1.

Visits for documentation will be abbreviated as follows:
V1=Screening visit (20 to 10 days before baseline)
V2=Baseline visit (week 0)
V3=Interim visit (week 2)
V4=Interim visit (week 4)
V5=Interim visit (week 8)
V6=End of treatment (EOT)/withdrawal visit (week 12)
V7=Follow-up (FU) visit (4 weeks after EOT/withdrawal visit)

Treatment groups will be abbreviated as follows:
N1500=6×250 mg Nor-UDCA capsules for oral use
N500=2×250 mg Nor-UDCA capsules for oral use and 4×250 mg placebo capsules
Placebo=6×250 mg placebo capsules The disposition and baseline demographic details of the study patients were as follows.

TABLE 1

Disposition of patients

| Disposition | Number of patients | | | |
|---|---|---|---|---|
| | N1500 | N500 | Placebo | Total |
| Randomized | 68 | 68 | 64 | 200 |
| Treated | 67 | 67 | 64 | 198 |
| Completed | 60 | 64 | 61 | 185 |
| Prematurely discontinued | 8 | 4 | 3 | 15 |
| Participated in FU phase | 67 | 64 | 63 | 194 |

TABLE 2

Summary of baseline demographic data

| | | Parameter | | | |
|---|---|---|---|---|---|
| | | N1500 (N =67) | N500 (N =67) | Placebo (N =64) | Total (N =198) |
| Gender | Male, n (%) | 40 (59.7%) | 45 (67.2%) | 38 (59.4%) | 123 (62.1%) |
| | Female, n (%) | 27 (40.3%) | 22 (32.8%) | 26 (40.6%) | 75 (37.9%) |
| Age (years) | Mean ± SD | 48.9 ± 12.8 | 44.9 ± 11.6 | 48.8 ± 11.4 | 47.5 ± 12.1 |
| BMI (kg/m$^2$) | Mean ± SD | 29.5 ± 4.8 | 30.6 ± 5.7 | 30.5 ± 5.3 | 30.2 ± 5.3 |

Example 1: Ultrasound Examination of the Liver

Method:

The ultrasound examination was performed at V1 or within 4 weeks before and 1 week after V1 and at V6. The following aspects were examined in particular:

Liver: size, echogenicity, overall finding (normal, abnormal—not clinically significant, abnormal—clinically significant.

Steatosis hepatis was assessed on a four-point scale, according to the following stages:

No/minimal steatosis: Normal liver echotexture was recorded in the absence of steatosis, or: Minimal steatosis was indicated by a slightly increased liver echogenicity in relation to the right kidney, but echogenicity of the intrahepatic vessel walls and diaphragm was well visualized.

Mild steatosis: Defined by a liver echogenicity moderately greater than the right kidney with slight decreased visibility of the intrahepatic vessel walls and decreased reflectivity of the hemidiaphragm.

Moderate steatosis: Defined by liver echogenicity moderately greater than the right kidney with poor visualization of intrahepatic vessel walls and decreased reflectivity of the hemidiaphragm.

Severe steatosis: Defined by a significantly increased echogenicity of the liver compared to the right kidney, a lack of visualization of intrahepatic vessel walls, and markedly decreased reflectivity of the hemidiaphragm.

The liver was scored by the most affected area.

Results:

The results are summarized in table 3. The percentage of patients with severe steatosis in the group receiving 1,500 mg Nor-UDCA decreased from 20.3% to 10.9%. In the group receiving 500 mg Nor-UDCA the percentage decreased from 27.3% to 16.7%. In the placebo group there was almost no change in the percentage of patients having severe steatosis.

This confirms that Nor-UDCA is effective in treating hepatic steatosis, in particular severe hepatic steatosis.

TABLE 3

Ultrasound examinations of the liver
Number (%) of patients

| | N1500 V1 (N = 67) | | N1500 V6 (N = 67) | | N500 V1 (N = 67) | | N500 V6 (N = 67) | | Placebo V1 (N = 64) | | Placebo V6 (N = 63) | |
|---|---|---|---|---|---|---|---|---|---|---|---|---|
| Parameter | n | % | n | % | n | % | n | % | n | % | n | % |
| Steatosis hepatis grade | | | | | | | | | | | | |
| No/minimal steatosis (S0) | 0 | 0.0 | 0 | 0.0 | 4 | 6.1 | 2 | 3.0 | 1 | 1.6 | 1 | 1.6 |
| Mild steatosis (S1) | 17 | 26.6 | 17 | 26.6 | 14 | 21.2 | 19 | 28.8 | 16 | 25.0 | 18 | 29.5 |
| Moderate steatosis (S2) | 34 | 53.1 | 40 | 62.5 | 30 | 45.5 | 34 | 51.5 | 35 | 54.7 | 31 | 50.8 |
| Severe steatosis (S3) | 13 | 20.3 | 7 | 10.9 | 18 | 27.3 | 11 | 16.7 | 12 | 18.8 | 11 | 18.0 |
| Missing | 3 | | 3 | | 1 | | 1 | | 0 | | 2 | |

Example 2: Liver Stiffness According to Fibroscan or ARFI in the Course of the Study Methods:
A) If available, Fibroscan examinations were performed at V1 or within 4 weeks before and 1 week after V1 and at V6. For the purpose of this measurement, patients should be fasting.

Liver Stiffness Measurement/Transient Elastography

Fibroscan is a non-invasive device (Echosens, France) for the detection steatosis hepatis by vibration-controlled transient elastography. It consists of a vibrator device coupled to an ultrasound system. The signal from this device allows a calculation of stiffness of scanned tissue, and thereby an assessment of the extent of disease. Results of liver elasticity are to be expressed by stiffness (kPa) and success rate (%).

During measurement, an ultrafast pulse echosequence is emitted (pulse repetition frequency of 6 kHz) during the propagation of the controlled shear wave. The acquisition lasts only 80 ms and strains induced in the liver by the propagation of the shear wave is measured using standard autocorrelation approach between successive ultrasound lines. Stiffness values were obtained in kPA.

Liver stiffness was measured using either of two probes (M-probe or XL-probe) and documented with the following respective thresholds for different stages:

M-Probe:
Stage 0/1 (i.e. <stage 2): <7.0 kPa (threshold)
Stage ≥2: ≥7.0 kPa
Stage ≥3: ≥8.8 kPa
Stage=4: ≥10.3 kPa XL-Probe:
Stage 0/1 (i.e. <stage 2): <6.2 kPa (threshold)
Stage ≥2: ≥6.2 kPa
Stage ≥3: ≥7.2 kPa
Stage=4: ≥7.9 kPa B) If available, Acoustic radiation force impulse imaging (ARFI) examinations were performed at V1 or within 4 weeks before and 1 week after V1 and at V6. ARFI measurements were documented with the following thresholds for different stages:
Stage 0/1 (i.e. <stage 2): <1.34 m/s (threshold)
Stage ≥2: ≥1.34 m/s
Stage ≥3: ≥1.55 m/s
Stage=4: ≥1.8 m/s Results:
As shown in table 4, the percentage of patients having a liver stiffness of stage 0 or 1 increased in the group receiving 1,500 mg Nor-UDCA from 55.6% to 67.5%. In the group receiving 500 mg Nor-UDCA and on the placebo group the percentage of patients with stage 0/1 liver stiffness decreased.

As a high liver stiffness is indicative of poor liver status, the results suggest that administration of 1,500 mg Nor-UDCA per day improves liver function.

TABLE 4

Liver stiffness according to Fibroscan or ARFI in the course of the study

Number (%) of patients

| | N1500 (N = 67) | | | | N500 (N = 67) | | | | Placebo (N = 64) | | | |
|---|---|---|---|---|---|---|---|---|---|---|---|---|
| | V1 | | V6-LOCF | | V1 | | V6-LOCF | | V1 | | V6-LOCF | |
| Category | n | % | n | % | n | % | n | % | n | % | n | % |
| Liver stiffness | | | | | | | | | | | | |
| Stage 0/1 | 20 | 55.6 | 27 | 67.5 | 30 | 62.5 | 28 | 58.3 | 24 | 72.7 | 22 | 61.1 |
| Stage ≥2 | 6 | 17.6 | 5 | 12.5 | 7 | 14.6 | 11 | 22.9 | 0 | 0.0 | 7 | 19.4 |
| Stage ≥3 | 3 | 8.3 | 2 | 5.0 | 5 | 10.4 | 4 | 8.3 | 1 | 3.0 | 2 | 5.6 |
| Stage = 4 | 7 | 19.4 | 6 | 15.0 | 6 | 12.5 | 5 | 10.4 | 8 | 24.2 | 5 | 13.9 |
| Missing | 31 | | 27 | | 19 | | 19 | | 31 | | 28 | |

Example 3: Hepatic Fat Fraction Measured by MRI and/or MRS

Method:

If available, magnetic resonance imaging/spectroscopy (MRI/MRS) examinations were performed at V1 or within 4 weeks before and 1 week after V1 and at V6. Both, MRI and MRS are MR-based methods to separate the liver signal into its water and fat components. The resonance frequencies corresponding to protons in water and to the dominant protons in fat are distinct, and can be quantified directly from the spectral tracing.

The following equation was to be used to calculate the hepatic fat fraction derived from chemical shift imaging (CSI) data:

$$\text{CSI hepatic fat fraction}_{uncorrected} = SI_{in\ phase} - SI_{opposed\ phase}/2 \times SI_{in\ phase}$$

To account for signal intensity differences not dependent of the fat content, a region of interest was also placed in the spleen in the same image as the liver measurements were performed. To calculate the signal-intensity corrected (using the spleen measurements) hepatic fat fraction, the equation above will be adopted as follows:

$$\text{CSI hepatic fat fraction}_{spleen\ correction} = (SI_{in\ phase\ liver}/SI_{spleen}) - (SI_{opposed\ phase\ liver}/SI_{spleen})/2 \times (SI_{in\ phase\ liver}/SI_{spleen})$$

If the calculations lead to negative mean hepatic fat fraction values, these negative values were considered as a fat fraction of 0, because a negative value is not possible.

MRS were performed at 1.5 or 3.0 Tesla to determine hepatic triglyceride content (in %).

Results:

The mean hepatic fat fraction, as determined by MRI, was reduced from 21.3% to 16.3% in the group receiving 1,500 mg Nor-UDCA. In the group receiving 500 mg and in the placebo group no substantial decrease in the hepatic fat fraction could be observed (see table 5).

TABLE 5

Hepatic fat fraction measured by MRI and/or MRS

| Visit | N1500 (N = 67) | | N500 (N = 67) | | Placebo (N = 64) | |
| --- | --- | --- | --- | --- | --- | --- |
| | N | Mean ± SD | N | Mean ± SD | N | Mean ± SD |
| V1 | 8 | 21.3 ± 15.4 | 7 | 14.6 ± 14.5 | 5 | 17.0 ± 12.3 |
| V6-LOCF | 8 | 16.3 ± 14.4 | 8 | 15.5 ± 13.5 | 5 | 16.0 ± 13.7 |

Example 4: Liver Enzymes

Methods:

The effects of Nor-UDCA on liver enzyme values have been assessed with respect to the courses of ALT, AST, GGT, AP and serum bilirubin. In addition, treatment effects with respect to pre-defined outcome criteria based on the upper limits of normal (ULN) of ALT, AST and GGT were examined.

The serum levels of ALT, AST, GGT, AP and serum bilirubin were determined by established standard laboratory methods.

Results:

For the liver enzyme parameters ALT, AST and GGT treatment effects of Nor-UDCA could be observed. The mean absolute change of ALT from V2 to V6-LOCF differed considerably between the treatment groups, showing a statistically significant decrease under N1500 (−17.2 U/l), a moderate decrease under N500 (−7.0 U/l) and a slight increase under Placebo (5.3 U/l).

A moderate dose dependency could also be observed for the change of AST (N1500: −8.7 U/l, N500: −3.8 U/l, Placebo: −0.9 U/l) and ALT/AST ratio (N1500: −0.14, N500: −0.05, Placebo: 0.10).

With respect to the course of GGT a clear and dose depending effect of treatment with Nor-UDCA was seen: patients under N1500 showed a distinct GGT decrease from 178.8 U/l at V2 to 111.7 U/l at V6-LOCF, while GGT values decreased only slightly under N500 (V2: 144.7 U/l, V6-LOCF: 137.6 U/l) and remained nearly unchanged under Placebo (V2: 150.0 U/l, V6-LOCF: 152.9 U/l).

There were no relevant differences observed in the course of AP and serum bilirubin values between N1500, N500 and Placebo.

Distinct and dose depending treatment effects of Nor-UDCA could be observed for the outcome criteria ALT≤0.8 ULN for patients with ALT>0.8 at baseline (N1500: 17.5%, N500: 14.8%, Placebo: 5.2%), ALT<ULN for patients with ALT>1.0 at baseline (N1500: 35.7%, N500: 16.9%, Placebo: 7.5%) and ALT<1.5 ULN for patients with ALT>1.5 at baseline (N1500: 53.1%, N500: 37.9%, Placebo: 24.1%).

With respect to AST, dose depending differences between treatment groups were visible for the criterion AST>0.33 ULN to ≤0.67 ULN (N1500: 32.7%, N500: 26.4%, Placebo: 6.9%). For the criteria AST<ULN (N1500: 54.5%, N500: 27.3%, Placebo: 37.9%) and AST<1.5 ULN (N1500: 75.0%, N500: 50.0%, Placebo: 66.7%) the proportion of patients fulfilling the criterion was higher with N1500 compared to N500 or Placebo.

More patients under Nor-UDCA than under Placebo experienced an improvement with respect to the combined criterion of ALT and/or AST decrease 15% (N1500: 71.6%, N500: 49.3%, Placebo: 35.9%).

A dose dependent effect of Nor-UDCA was observed with respect to the outcome criterion GGT>0.33 ULN to ≤0.67 (N1500: 21.6%, N500: 13.0%, Placebo: 7.4%). Regarding GGT ULN, the proportion of patients under N1500 was highest (31.0%), while between N500 (12.2%) and Placebo (14.0%) no relevant differences were observed.

A description of the course of liver enzyme values in the FAS over the study is provided in table 5.

TABLE 5

Liver enzyme values in the course of the study

| Liver enzyme/ Visit | N1500 (N = 67) | | N500 (N = 67) | | Placebo (N = 64) | |
| --- | --- | --- | --- | --- | --- | --- |
| | N | Mean ± SD | N | Mean ± SD | N | Mean ± SD |
| ALT (U/l) | | | | | | |
| V2 | 63 | 78.6 ± 34.2 | 66 | 80.3 ± 33.3 | 63 | 77.4 ± 30.2 |
| V3 | 65 | 72.8 ± 33.1 | 66 | 79.4 ± 40.6 | 63 | 80.8 ± 42.3 |
| V4 | 64 | 62.6 ± 24.7 | 65 | 75.2 ± 34.6 | 64 | 75.6 ± 35.2 |
| V5 | 60 | 62.0 ± 27.9 | 65 | 75.6 ± 36.8 | 62 | 78.0 ± 32.9 |
| V6 | 60 | 62.8 ± 29.1 | 64 | 70.8 ± 31.6 | 60 | 82.3 ± 47.6 |
| V6 (LOCF) | 67 | 61.8 ± 28.3 | 67 | 72.8 ± 33.2 | 64 | 82.3 ± 46.7 |
| V6 (LOCF)-V2 | 67 | −17.2 ± 23.3 | 67 | −7.0 ± 27.4 | 64 | 5.3 ± 41.0 |
| AST (U/l) | | | | | | |
| V2 | 63 | 49.3 ± 25.1 | 66 | 49.8 ± 27.4 | 63 | 51.6 ± 23.5 |
| V3 | 65 | 43.7 ± 15.7 | 66 | 47.9 ± 22.4 | 63 | 50.2 ± 21.0 |

TABLE 5-continued

Liver enzyme values in the course of the study

| Liver enzyme/ Visit | N1500 (N = 67) | | N500 (N = 67) | | Placebo (N = 64) | |
|---|---|---|---|---|---|---|
| | N | Mean ± SD | N | Mean ± SD | N | Mean ± SD |
| V4 | 64 | 42.6 ± 19.9 | 65 | 46.0 ± 18.8 | 64 | 48.6 ± 18.6 |
| V5 | 60 | 40.5 ± 16.3 | 65 | 46.9 ± 24.4 | 62 | 50.1 ± 21.0 |
| V6 | 60 | 41.3 ± 19.8 | 64 | 43.9 ± 20.4 | 60 | 49.3 ± 24.1 |
| V6 (LOCF) | 67 | 40.8 ± 19.1 | 67 | 45.6 ± 24.7 | 64 | 50.4 ± 24.8 |
| V6 (LOCF)-V2 | 67 | −8.7 ± 13.6 | 67 | −3.8 ± 14.3 | 64 | −0.9 ± 19.3 |
| ALT/AST | | | | | | |
| V2 | 63 | 1.68 ± 0.53 | 66 | 1.71 ± 0.50 | 63 | 1.60 ± 0.56 |
| V3 | 65 | 1.66 ± 0.41 | 66 | 1.70 ± 0.51 | 63 | 1.67 ± 0.64 |
| V4 | 64 | 1.53 ± 0.41 | 65 | 1.67 ± 0.48 | 64 | 1.60 ± 0.54 |
| V5 | 60 | 1.54 ± 0.34 | 65 | 1.66 ± 0.47 | 62 | 1.65 ± 0.56 |
| V6 | 60 | 1.55 ± 0.34 | 64 | 1.66 ± 0.45 | 60 | 1.72 ± 0.57 |
| V6 (LOCF) | 67 | 1.54 ± 0.34 | 67 | 1.67 ± 0.48 | 64 | 1.70 ± 0.57 |
| V6 (LOCF)-V2 | 67 | −0.14 ± 0.42 | 67 | −0.05 ± 0.37 | 64 | 0.10 ± 0.40 |
| GGT (U/l) | | | | | | |
| V2 | 64 | 178.8 ± 205.6 | 66 | 144.7 ± 160.0 | 63 | 150.0 ± 140.8 |
| V3 | 66 | 170.1 ± 217.9 | 66 | 151.9 ± 166.4 | 63 | 146.6 ± 141.1 |
| V4 | 64 | 128.5 ± 126.1 | 65 | 138.9 ± 141.6 | 64 | 135.7 ± 130.4 |
| V5 | 60 | 111.5 ± 112.7 | 65 | 133.6 ± 124.2 | 62 | 143.9 ± 155.2 |
| V6 | 60 | 109.6 ± 115.8 | 64 | 139.2 ± 147.6 | 61 | 154.2 ± 169.9 |
| V6 (LOCF) | 67 | 111.7 ± 116.3 | 67 | 137.6 ± 144.8 | 64 | 152.9 ± 166.2 |
| AP (U/l) | | | | | | |
| V2 | 64 | 92.0 ± 36.6 | 66 | 83.9 ± 27.6 | 63 | 94.3 ± 32.1 |
| V3 | 66 | 95.4 ± 40.1 | 66 | 88.3 ± 34.3 | 63 | 94.1 ± 39.7 |
| V4 | 64 | 90.9 ± 32.0 | 65 | 86.5 ± 34.3 | 64 | 92.6 ± 35.8 |
| V5 | 60 | 91.1 ± 33.3 | 65 | 86.1 ± 30.0 | 62 | 92.6 ± 32.7 |
| V6 | 60 | 92.9 ± 31.3 | 64 | 87.4 ± 32.7 | 61 | 95.6 ± 38.5 |
| V6 (LOCF) | 67 | 91.8 ± 32.1 | 67 | 86.9 ± 32.2 | 64 | 94.7 ± 38.0 |
| Serum bilirubin (mg/dl) | | | | | | |
| V2 | 61 | 0.61 ± 0.32 | 65 | 0.64 ± 0.40 | 62 | 0.57 ± 0.47 |
| V3 | 64 | 0.52 ± 0.26 | 64 | 0.63 ± 0.38 | 61 | 0.57 ± 0.38 |
| V4 | 60 | 0.53 ± 0.26 | 64 | 0.61 ± 0.38 | 62 | 0.56 ± 0.39 |
| V5 | 60 | 0.54 ± 0.28 | 65 | 0.64 ± 0.41 | 59 | 0.54 ± 0.46 |
| V6 | 60 | 0.56 ± 0.32 | 60 | 0.62 ± 0.36 | 58 | 0.59 ± 0.39 |
| V6 (LOCF) | 67 | 0.57 ± 0.31 | 67 | 0.62 ± 0.38 | 64 | 0.58 ± 0.38 |
| V6 (LOCF)-V2 | 66 | −0.03 ± 0.20 | 67 | −0.01 ± 0.22 | 64 | 0.02 ± 0.24 |

Example 5: Cytokeratin 18 in the Course of the Study

The mean values of Cytokeratin 18 (M30 fragment) at V2 were on similar levels over the treatment groups (N1500: 333.7 U/I, N500: 389.4 U/I, Placebo: 357.6 U/I). During the study, these values decreased comparably in all treatment groups (N1500: −30.3 U/I, N500: −34.4 U/I, Placebo: −29.3 U/I).

Also the mean values of Cytokeratin 18 (M65 fragment) were similar in all groups at V2 (N1500: 519.9 U/I, N500: 590.2 U/I, Placebo: 584.2 U/I). During the study, the mean value decreased more in the N500 group (−106.0 U/I) than in the N1500 (−80.6 U/I) or Placebo group (−34.6 U/I).

The invention claimed is:

1. A method of treating hepatic steatosis with Nor-UDCA, wherein said treating comprises administering to a human patient in need thereof which has not yet progressed to steatohepatitis an effective amount of Nor-UDCA, and wherein said human patient has a hepatic fat fraction of greater than 20%, wherein the Nor-UDCA is administered to the patient once per day, wherein the dose of Nor-UDCA administered to the human patient is from 1,000 mg/day to 2,500 mg/day, wherein said treating reduces the hepatic fat fraction of the patient by at least 2 percentage points, and wherein said human patient does not show signs of inflammation or hepatitis.

2. The method of treating hepatic steatosis with Nor-UDCA according to claim 1, wherein the patient has moderate steatosis or severe steatosis.

3. The method of treating hepatic steatosis with Nor-UDCA according to claim 1, wherein the patient has a serum concentration of alanine transaminase (ALT) which is from 0.8-fold of the upper limit of normal (ULN) to less than 4 times the ULN.

4. The method of treating hepatic steatosis with Nor-UDCA according to claim 3, wherein the treating reduces the serum concentration of ALT to less than the ULN.

5. The method of treating hepatic steatosis with Nor-UDCA according to claim 4, wherein the treating reduces the serum concentration of ALT to less than, or equal to, 0.9 times the ULN.

6. The method of treating hepatic steatosis with Nor-UDCA according to claim 4, wherein the treating reduces the serum concentration of ALT to less than, or equal to, 0.8 times the ULN.

7. The method of treating hepatic steatosis with Nor-UDCA according to claim 1, wherein the patient has a serum concentration of aspartate transaminase (AST) which is less than 4 times the upper limit of normal (ULN).

8. The method of treating hepatic steatosis with Nor-UDCA according to claim 1, wherein said treating reduces the hepatic fat fraction of the patient by at least 10%.

9. The method of treating hepatic steatosis with Nor-UDCA according to claim 1, wherein the body mass index of the patient is greater than 25 kg/m$^2$.

10. The method of treating hepatic steatosis with Nor-UDCA according to claim 1, wherein the dose of Nor-UDCA administered to the patient is from about 1000 mg/day to about 1,500 mg/day.

11. The method of treating hepatic steatosis with Nor-UDCA according to claim 10, wherein the dose of Nor-UDCA administered to the patient is about 1,500 mg/day.

12. The method of treating hepatic steatosis with Nor-UDCA according to claim 1, wherein the Nor-UDCA is administered orally to the patient.

13. The method of treating hepatic steatosis with Nor-UDCA according to claim 1, wherein said treating further comprises administering an active agent different from Nor-UDCA, wherein said active agent different from Nor-UDCA is selected from the group consisting of antifibrotic agents, anti-inflammatory agents, immunomodulators, biologics, cholesterol reducing substances, leukotriene antagonists and combinations thereof.

14. The method of treating hepatic steatosis with Nor-UDCA according to claim 13, wherein said active agent different from Nor-UDCA is selected from the group consisting of pirfenidone, fibrates, budesonide, fluticasone, flunisolide, ciclisonide, mometasone, beclomethasone and combinations thereof.

15. The method of treating hepatic steatosis with Nor-UDCA according to claim 1, wherein the treating results in reducing liver fat in the patient.

16. The method of treating hepatic steatosis with Nor-UDCA according to claim 1, wherein said Nor-UDCA is a polymorph characterized by XRPD peaks at 11.9, 14.4, 15.3, 15.8, and 16.6±0.2 degrees of 2-theta.

* * * * *